United States Patent [19]
Koerts et al.

[11] Patent Number: 5,378,834
[45] Date of Patent: Jan. 3, 1995

[54] PROCESS FOR PURIFYING PRODUCTS CONTAINING ESTERS OF A NON-REDUCING SUGAR AND ONE OR MORE FATTY ACIDS

[75] Inventors: Kees Koerts, Driebergen; Age Bakker, Oosterhout; Gerardus M. Vianen, Roosendaal, all of Netherlands

[73] Assignee: Cooperatieve Vereniging Suiker Unie U.A., Netherlands

[21] Appl. No.: 91,457

[22] Filed: Jul. 14, 1993

Related U.S. Application Data

[63] Continuation of Ser. No. 540,831, Jun. 20, 1990, abandoned.

[30] Foreign Application Priority Data

Jun. 22, 1989 [NL] Netherlands .......................... 8901578

[51] Int. Cl.$^6$ .................... C07H 17/00; C07H 13/02; C07H 11/00; C07H 15/04
[52] U.S. Cl. .................................. 536/127; 536/119; 536/124; 536/115; 536/116; 536/120; 560/84; 560/85
[58] Field of Search ................ 536/127, 119, 124, 115, 536/116, 120; 560/84, 85

[56] References Cited

U.S. PATENT DOCUMENTS

| | | | |
|---|---|---|---|
| 4,377,686 | 3/1983 | Feuge et al. | 536/119 |
| 4,601,856 | 7/1986 | Suzuki et al. | 554/202 |
| 4,675,132 | 6/1987 | Stout et al. | 554/202 |
| 4,778,881 | 10/1988 | Nieuwenhuis et al. | 536/119 |
| 4,973,681 | 11/1990 | Watanabe | 536/119 |
| 4,973,682 | 11/1990 | Willemse | 536/119 |
| 5,001,224 | 3/1991 | Barstow et al. | 530/334 |

FOREIGN PATENT DOCUMENTS 0065390 6/1982 European Pat. Off. .
8901578 6/1989 Netherlands .

OTHER PUBLICATIONS

Ullmanns' Enclyclopedie der Technischen Chemie, Band 24, p. 753 (1983) 4th Edition.
Kirk-Othmer Encyclopedia of Chemical Technology, 3.Ed. Supp vol, pp. 872–883 (1984).
Analytical Chemistry, vol. 57, 1985, pp. 2243–2247, entitled "Separation of Sucrose Polyesters by Capillary Supercritical-Fluid Chromatography/Flame Ionization Detection with Robot-Pulled Capillary Restrictors", by T. L. Chester et al.

Primary Examiner—Michael G. Wityshyn
Assistant Examiner—Louise N. leary
Attorney, Agent, or Firm—Webb Ziesenheim Bruening Logsdon Orkin & Hanson

[57] ABSTRACT

The invention relates to a process for purifying crude products containing esters of a non-reducing sugar like sucrose, and one or more fatty acids such as palmitic acid, stearic acid etc. by subjecting the crude esterification products to an extraction treatment with supercritical carbon dioxide. After carrying out this extraction treatment a residue comprising the fatty acid esters of non-reducing sugars, the unreacted sugar and the salts as well as an extract comprising the fatty acids, fatty acid alkyl esters and also any solvents, if present, are obtained. The unreacted sugar and the salts, present in the obtained residue, can be removed from the residue by, for example, a washing operation resulting in a final product of pure esters of the non-reducing sugar and one or more fatty acids. This last removal step concerning the unreacted sugar and salts may also be carried out before the application of the above indicated extraction treatment with supercritical carbon dioxide.

14 Claims, 1 Drawing Sheet

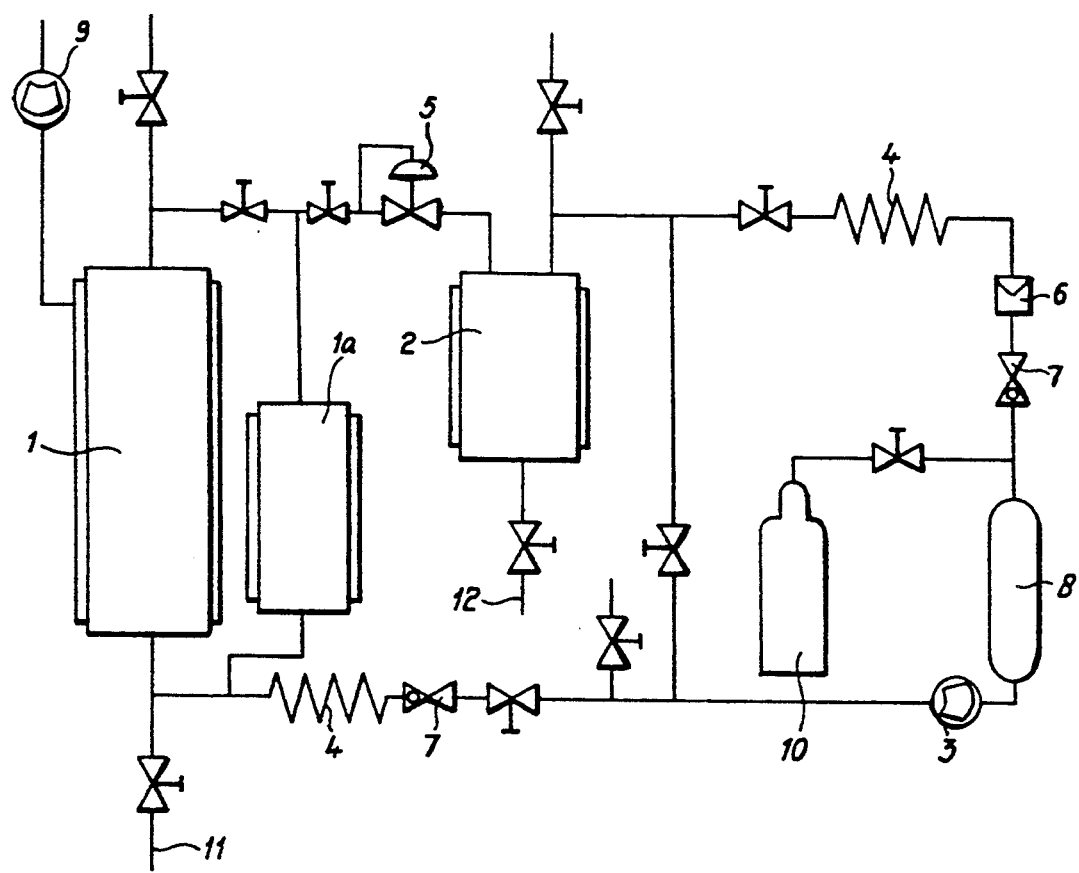

PROCESS FOR PURIFYING PRODUCTS CONTAINING ESTERS OF A NON-REDUCING SUGAR AND ONE OR MORE FATTY ACIDS

This is a continuation of copending application Ser. No. 07/540,831 filed on Jun. 20, 1990, now abandoned.

The invention relates to a process for purifying products containing esters of a non-reducing sugar, such as sucrose, and one or more fatty acids, such as palmitic acid, stearic acid, etc.

As is known, esters of a non-reducing sugar and one or more fatty acids, in particular the monoesters and diesters derived from such a sugar, are valuable surfactants which have unique advantages because of their composition. Such fatty acid esters of a non-reducing sugar can be used as emulsifier in foodstuffs, cosmetics, pharmaceutical preparations and also agricultural products. In addition to the monoesters and diesters, polyesters are also known whose degree of substitution exceeds 2 and which therefore contain, for example, 4 of more fatty acid units per monosaccharide unit. Such polyesters are known, inter alia, because of their use in the treatment of hypercholesterolaemia. Said polyesters can also be used as noncalorific fat substitutes.

More particularly, fatty acid monoesters and diesters of, inter alia, sucrose can be prepared in many ways. However, all these methods yield final products which can be converted into pure fatty acid esters of sucrose in sufficiently high yield and with a sufficient purity only by making great efforts. The most conventional process, which is known from U.S. Pat. No. 2,893,990, relates to the transesterification of a non-reducing sugar with the methyl ester of a fatty acid such as methyl stearate, in dimethyl sulphoxide or dimethylformamide as solvent and with potassium carbonate as catalyst. The working up of the reactions products obtained in this way in order to obtain purified fatty acid esters of such non-reducing sugars is accompanied in practice by great difficulties. A complete or partial removal of the toxicologically undesirable dimethyl sulphoxide or dimethylformamide by distillation followed by washing operations with water or organic solvents results in the desired purity only after repeated washing operations. However, these methods of working up are accompanied by substantial losses of the desired product.

The purification of fatty acid monoesters and diesters of, for example, sucrose which have been prepared by the microemulsion method, which method is described in U.S. Pat. No. 3,480,616 and 3,644,333, or via homogeneous melting processes, which processes are reported in U.S. Pat. No. 4,3792,041 and British Patent Specification 2,081,266, is characterized by the laborious removal of the co-emulsifiers required with these processes. Said co-emulsifiers and potassium soaps, sodium soaps and lithium soaps of fatty acids containing 6–22 carbon atoms.

Further, U.S. Pat. No. 4,748,324 reports possibilities of obtaining fatty acid ester products of non-reducing sugars from crude reaction mixtures and the like. Apart from the known methods discussed in this U.S. Patent Specification, this patent specification relates to a purification of fatty acid esters of sucrose from crude reaction mixtures by precipitating the fatty acids as, for example, $Ca^{2+}$ salts from an organic solvent. Other possibilities are repeated crystallizations, with or without adding salts, from organic solvents such as methyl ethyl ketone. However, these purification methods are characterized, on the one hand, by a waste flow of calcium salts of fatty acids, for which an expensive recycling is necessary for reasons of process economics, and on the other hand, by losses of desired sugar esters.

To summarize, it can be stated that the methods known from the prior art for purifying fatty acid monoesters and diesters of non-reducing sugars from crude reaction mixtures are characterized, on the one hand, by complicated operations for removing toxic solvents such as dimethyl sulphoxide and dimethylformamide or other toxic solvents, or by substantial losses of the desired sugar esters and also a laborious processing in relation to removing the salts of the fatty acids.

In addition to fatty acid monoesters and diesters of non-reducing sugars, fatty acid esters of non-reducing sugars having a higher degree of substitution can also be prepared. Examples of such methods are described, inter alia, in European Patent Specification 256,585, British Patent Specification 2,161,806 and in J.A.O.C.S. 66, (1978), pages 398–401. The reaction products prepared according to the above described literature references are characterized by the presence of fatty acid soaps which are necessary in this processing as co-emulsifier or have been produced by saponification, or a considerable quantity of fatty acid alkyl ester such as methyl stearate which has to be present in excess during the reaction. To remove the two last-mentioned components from the reaction product, for example, a solvent extraction is proposed, but this is economically disadvantageous. For example, inter alia, large quantities of organic solvent such as methanol are necessary in this case. Other methods of purifying the sugar esters such as, for example, the molecular distillation proposed in British Patent Specification 2,161,806 can only be carried out with difficulty in practice due to the presence of salts. Said salts are formed by the neutralization of the basic reaction product before subjecting it to a molecular distillation.

To summarize, it may be stated that the fatty acid esters of non-reducing sugars having a higher degree of esterification than the fatty acid monoesters and diesters can also be purified in practice only with large losses or by laborious methods which are difficult to carry out in practice.

The Applicant has therefore sought a method for purifying the crude esterification product of a non-reducing sugar and one or more fatty acids in which the abovementioned problems have been completely or large eliminated.

It was found that the object stated above can be achieved if the crude esterification product of a non-reducing sugar and one or more fatty acids is subjected to an extraction treatment with supercritical carbon dioxide. In the case of crude esterification products which also contain one or more alkali-metal soaps of fatty acids, they are acidified prior to the extraction treatment with supercritical $CO_2$; this additional step is explained in more detail below.

More particularly, the liquid properties of the supercritical $CO_2$ can be varied, by adjusting the pressure and the temperature, in a manner such that an optimum separation between the components in the crude esterification product can be achieved. The solubility of the components to be extracted in supercritical $CO_2$ can possibly be increased by adding "co-solvents" such as, for example, ethyl acetate, methyl ethyl ketone, lower alcohols and water. In the process according to the invention, the fatty acid esters of non-reducing sugars, the unreacted sugar and the salts remain behind after the extraction with supercritical carbon dioxide, while the fatty acids and the fatty acid alkyl esters, and also any solvents present such as, for example, dimethyl sulphoxide and dimethylformamide, are extracted.

The supercritical carbon dioxide extraction medium is particularly attractive since it is nonflammable, nonexplosive and, in addition, leaves no traces behind in the treated product. In addition, supercritical carbon dioxide is toxicologically safe and is therefore accepted in the foodstuffs industry.

The method according to the invention can be used for all types of esterification products, regardless of the method of preparation thereof. For example, a reaction product known from U.S. Pat. No. 2,893,990 in dimethyl sulphoxide, dimethylformamide or another characteristic solvent can be extracted after neutralisation batchwise with supercritical carbon dioxide (temperature $<31°$ C.; pressure $>72.9$ bar). In this process, the solvent concerned and also the fatty acid formed by saponification and the residual alkyl fatty acid esters dissolve. The losses of sugar esters are in this case zero. The carbon dioxide in the carbon dioxide extract, which contains fatty acids, fatty acid alkyl esters and the solvent used during the reaction, can be re-used after removal. The extraction of the fatty acids is accelerated by acidifying the crude reaction product. In this connection it is pointed out that alkali-metal soaps of fatty acids are hardly soluble in supercritical $CO_2$. The residue left behind in the extraction with supercritical carbon dioxide no longer contains any detectable quantities of the reaction solvent such as dimethyl sulphoxide. In addition, the salts and the sugars can be removed from said residue by, for example, a washing operation involving acidified water, with the result that a final product of pure esters of the non-reducing sugar and one or more fatty acids is obtained.

The crude reaction products which are obtained in carrying out the microemulsion methods (U.S. Pat. Nos. 3,408,616 and 3,644,333) and the homogeneous melting processes (see U.S. Pat. No. 3,792,041 and British Patent Specification 2,081,266) are acidified to a pH of less than 7, preferably between 4 and 5. Examples of acids to be used are hydrogen chloride, sulphuric acid, phosphoric acid, formic acid, acetic acid, lactic acid, succinic acid, sodium hydrogensulphate, sodium dihydrogenphosphate and the corresponding acids. In this way, the potassium soaps, sodium soaps and lithium soap of the fatty acids are converted into the corresponding fatty acids and salts. The acidified reaction product obtained in this process is then subjected to an extraction treatment with supercritical carbon dioxide.

The residue obtained in this process can be further worked up in the above manner, i.e. freed from salts and sugars.

More generally, it may be stated that the abovementioned extraction treatment with supercritical carbon dioxide must be carried out at a temperature of at least 31° C. and advantageously at less than 170° C. and preferably between 40° and 100° C. The upper limit of 170° C. is related to the phenomenon that sugar esters start to exhibit decomposition phenomena above 170° C. The pressure used in the extraction according to the invention is at least 72.9 bar. The upper limit of the pressure range depends on the limits imposed on the equipment used, but is usually approximately 600 bar. Preferably, a pressure in the range of 150–450 bar is used. In addition, the weight ratio of the crude esterification product containing palmitic or stearic acid to supercritical $CO_2$ is in the range of, for example, 1:25 to 1:500, advantageously 1:50 to 1:150. For an esterification product containing oleic acid or lauric acid, said weight ratio is considerably lower, i.e., in the range from 1:2.5 to 1:125, advantageously 1:5 to 1:15.

Under the above conditions, fatty acids containing 6–22 carbon atoms and also the lower alkyl esters derived therefrom are extracted in the extraction treatment with supercritical $CO_2$. After removal of the $CO_2$ from the extract obtained, said extract can be used for recycling. The residue obtained after the extraction treatment, which is composed of the desired fatty esters of non-reducing sugar and also of unreacted sugar and salts, can be freed from the unreacted sugar and the salts in a simple way after removal of the $CO_2$. One possible method comprises washing with (a) optionally acidified water or (b) washing with generally known slightly polar solvents such as, for example, ethanol, propanol, isopropanol, butanol, isobutanol, ethyl acetate, acetone or methyl ethyl ketone.

In connection with the above it is pointed out that the washing with optionally acidified water or with the said solvents can also be carried out prior to carrying out the extraction treatment with supercritical $CO_2$. A particular embodiment of the process according to the invention can therefore be carried out by freeing the crude reaction product from sugar and salts via, for example, a water/methyl ethyl ketone extraction at a pH of, for example, 4.5, then freeing the metal ethyl ketone fraction from the solvent and subsequently subjecting it to an extraction with supercritical carbon dioxide according to the invention, in which a separation between the sugar esters, on the one hand, and the fatty acids and fatty acid alkyl esters, on the other hand, if also effected.

The abovementioned water/methyl ethyl ketone extraction may also be replaced by extractions of the acidic crude reaction product with, for example, ethanol, propanol, isopropanol, butanol, isobutanol, ethyl acetate, acetone or methyl ethyl ketone.

In addition to working up crude esterification products containing fatty acid monoesters and diesters of non-reducing sugars, the fatty acid esters of non-reducing sugars having a higher degree of substitution of, for example, 4 or more are also obtained in the above way. In view of the nonpolar nature of such fatty acids of non-reducing sugars, said product is, however, also partially extracted by the supercritical carbon dioxide. In this connection, it is emphasized that the residue remaining behind in the extraction treatment with supercritical carbon dioxide is completely freed from fatty acid alkyl esters, which are quantitatively the greatest contaminant, and also from the fatty acid which is present as a co-emulsifier and as a result of saponification.

The fact that some of the fatty acid esters of non-reducing sugars having a high degree of substitution of, for example, 4 or more are extracted by means of the $CO_2$ extract implies, however, a loss in yield. This loss in yield can, however, largely be eliminated by returning said extract to the sugar-fatty acid ester preparation reaction.

The extraction treatment, with supercritical $CO_2$, of crude reaction products which contain fatty acid esters of non-reducing sugars having a higher degree of substitution is advantageously carried out continuously at a temperature at which the polyester is liquid.

BRIEF DESCRIPTION OF THE DRAWING

The FIGURE shows an apparatus for extraction treatment with supercritical $CO_2$, of crude reaction products which contain fatty acid esters of non-reducing sugars.

The extraction treatment with supercritical $CO_2$ to be carried out according to the invention may, for example, be carried out with the aid of an apparatus according to the accompanying FIGURE in the following manner. The crude reaction product containing the fatty acid esters of the non-reducing sugar is introduced into an extraction vessel 1 or 1a respectively. The compressor 3 pumps the carbon dioxide and raises it to an elevated pressure of, for example, 150 bar. The heat exchanger 4 then raises the carbon dioxide to the desired temperature, which is higher than the critical temperature of 31° C. The carbon dioxide rendered supercritical in this manner is then passed through the extraction vessel 1 or 1a respectively at a rate of, for example, 2.5 kg of carbon dioxide per hour. In this process, said supercritical carbon dioxide dissolves the extract concerned out of the crude basic material used. With the aid of the pressure regulation 5, the pressure is then reduced, as a result of which the solubility of the extracted product in the extract decreases and it deposits under these circumstances in the reservoir 2. The gaseous carbon dioxide obtained from the reservoir 2, which then virtually no longer contains any extracted substances, is then passed via heat exchanger 4, filter 6 and valve 7 to a condenser 8, after which the carbon dioxide, possibly after being topped up from the $CO_2$ reservoir 10, if fed back again via compressor 3 to the extraction column 1 or 1a respectively. The apparatus according to the FIGURE can be operated either continuously with an extraction column 1 or batchwise with the extraction column 1a. In carrying out a continuous extraction process, a crude product of fatty acid esters of the non-reducing sugar is fed via feed pump 9. The product treated with supercritical carbon dioxide is removed via pipe 11, while the extracted deposited in the reservoir 2 is removed via pipe 12.

The invention is explained in more detail with reference to the examples below. These examples should not be interpreted in a restrictive way.

EXAMPLE I

A reaction product obtained by the microemulsion technique was acidified in the reactor at 140° C. with acetic acid to a pH of 4.5. After cooling, the following composition was found:
Sucrose stearates: 43.5% by weight
Stearic acid: 19% by weight
Methyl stearate: 2.5% by weight
Sucrose and salts: 35% by weight An extraction with supercritical $CO_2$ was carried out with 50 g of ground product in the apparatus according to the accompanying FIGURE. A quantity of 4.25 kg of $CO_2$ was passed through at 40° C. and 170 bar at a flow rate of 2.5 kg $CO_2$/hour. After removal of the $CO_2$, the extract (10.2 g) contained 12% by weight of methyl stearate and 88% by weight of stearic acid. The residue (39.8 g) contained 54.7% by weight of sucrose stearates, 1.2% by weight of free fatty acid and also sucrose and salts. Said residue was washed (10% w/v) with 2-propanol at 60° C. After insoluble sucrose and salt had been separated off by filtration, the solution was evaporated to a dry product in a rotary vacuum evaporator. The dry product obtained contained 98% by weight of sucrose stearates and 2% by weight of stearic acid.

EXAMPLE II

A crude reaction product (100 parts by weight) prepared by a melt reaction process was extracted at a pH of 4.5 with 200 parts by weight of methyl ethyl ketone (MEK) and 100 parts by weight of water. The pH was adjusted with hydrochloric acid. After evaporating the MEK extract to dryness, a residue (71 parts by weight) was obtained which was composed of 64.8% by weight of sucrose palmitate, 32.4% by weight of palmitic acid and 2.8% by weight of methyl palmitate. 50 g of the said product were subjected to an extraction with supercritical $CO_2$ at 80° C. 3.4 kg of $CO_2$ were passed through at 370 bar at a flow rate of 2.5 kg $CO_2$/hour. The extract (17.1 g) contained 92% by weight of palmitic acid and 8% by weight of methyl palmitate. The residue (32.9 g) was composed of 98.5% by weight of sucrose palmitates and 1.5% by weight of palmitic acid.

EXAMPLE III

A crude reaction product obtained by reacting methyl oleate with sucrose in dimethyl sulphoxide (DMSO) in the presence of potassium carbonate was composed of 396 g of sucrose, 245 g of sucrose oleates (monoesters/diesters 50/50), 10 g of oleic acid and, because the mixture had been acidified with hydrochloric acid to a pH of 4.5 at the end of the reaction, 16 g of potassium chloride in 2000 ml of DMSO.

This mixture was evaporated with the aid of a rotary vacuum evaporator until only 200 g of DMSO remained. 50 g of the product obtained were extracted in the course of 2 hours with a total of 5.5 kg of $CO_2$ at 90° C. and 350 bar. The residue was composed of sucrose (23.4 g), potassium chloride (1.0 g) and sucrose oleates (14.5 g). No detectable quantity of DMSO (<2 ppm) could no longer be found in it. Said residue was then extracted with ethanol (10%, w/v). The insoluble sucrose and potassium chloride were separated off by filtration, after which the filtrate was evaporated to dryness with a rotary vacuum evaporator. The final product still contained 1% by weight of oleic acid, in addition to sucrose oleates (99% by weight). The $CO_2$ extract was composed of DMSO (11.8 g) and oleic acid (0.6 g) after removal of the $CO_2$.

EXAMPLE IV

A reaction product of a reaction between sucrose and methyl palmitate in the presence of potassium palmitate and potassium carbonate contained sucrose palmitate with a degree of substitution of 6.5. The reaction product was composed of 43.5% by weight of sucrose palmitate, 35.3% by weight of methyl palmitate, 17% by weight of palmitic acid and, after acidification to a pH of 4.5 with hydrochloric acid, 4.2% by weight of potassium chloride. 50 g of this product were extracted batchwise at 40° C. and 170 bar in the course of 1.5 hours with a total of 3.8 kg of $CO_2$. The residue obtained was composed of 15.2 g of sucrose palmitate (degree of substitution: 6.5), 0.6 g of palmitic acid and 2.1 g of KCl. The extract obtained after removal of the $CO_2$ was composed of 17.7 g of methyl palmitate, 7.9 g palmitic acid and 6.5 g of sucrose palmitate. The residue was washed out with hexane to remove the salt and sugar. After evaporating this filtrate to dryness, there remained 15.2 g of sucrose having a degree of substitution of 6.5. The $CO_2$ extract can be re-used without further treatment, with the result that the actual yield of the extraction is 100%.

EXAMPLE V

A reaction product obtained by the melting process was acidified in the reactor with acetic acid (pH of 10% suspension is 4.7). After cooling, the following composition was found:

Sucrose stearates: 45% by weight
Lauric acid: 18% by weight
Stearic acid: 1.5% by weight
Methyl stearate: 1.5% by weight
Sucrose and salts: 34% by weight 50 g of this product were subjected for 15 min to an extraction with supercritical $CO_2$ at 40° C. and 400 bar at a flow rate of 2.2 kg $CO_2$/hour. After removal of the carbon dioxide, the extract contained 10.1 g of solid matter (88% by weight of lauric acid, 4.5% by weight of stearic acid and 7.5% by weight of methyl stearate). The residue contained 56.4% by weight of sucrose stearates, 42.6% by weight of sucrose and salts, 0.8% by weight of stearic acid and 0.2% by weight of lauric acid. This residue was worked up further in the manner described in Example I, after which a 99% by weight of pure sucrose stearate was obtained.

We claim:

1. Process for purifying esterification products containing fatty acid esters of a non-reducing sugar comprising subjecting esterification products containing fatty acid esters of a non-reducing sugar to an extraction treatment with supercritical carbon dioxide, wherein said extraction treatment comprises the step of passing supercritical carbon dioxide through a reaction vessel containing said esterification products containing fatty acid esters of a non-reducing sugar, wherein said esterification products containing fatty acid esters of a non-reducing sugar and any unreacted sugar and any salts remain behind after the extraction with supercritical carbon dioxide and further wherein any unreacted fatty acids and any fatty acid alkyl esters, and any solvents present as such, are extracted with the supercritical carbon dioxide.

2. Process according to claim 1 wherein said products containing fatty acid esters of a non-reducing sugar, which also contain an alkali metal soap, are acidified and then subjected to an extraction treatment with supercritical carbon dioxide.

3. Process according to claim 2 wherein said products containing fatty acid esters of a non-reducing sugar are acidified with an agent selected from the group consisting of hydrogen chloride, sulphuric acid, phosphoric acid, sodium hydrogen sulphate and sodium dihydrogen phosphate.

4. Process according to claim 2 wherein said products are acidified to a pH of 4-5.

5. Process according to claim 4 wherein said extraction treatment with supercritical carbon dioxide is carried out at a temperature in the range of 31-170 degrees C. and under a pressure of 72.9-600 bar.

6. Process according to claim 5 wherein said extraction treatment with supercritical carbon dioxide is carried out at a temperature in the range of 40-100 degrees C. and under a pressure in the range of 150-450 bar.

7. Process according to claim 6 wherein residue obtained after the extraction treatment with supercritical carbon dioxide is subjected to a washing treatment with a washing medium selected from the group consisting of water and a slightly polar organic solvent.

8. Process according to claim 1 wherein said products are subjected, prior to said extraction treatment, to a washing treatment with a washing medium selected from the group consisting of water and a slightly polar organic solvent.

9. Process according to claim 8 wherein said slightly polar organic solvent is selected from the group consisting of ethanol, propanol, isopropanol, butanol, isobutanol, ethyl acetate, acetone and methyl ethyl ketone.

10. Process according to claim 9 wherein the ratio between said products and said supercritical carbon dioxide is 1:25 to 1:500 by weight and further wherein said products contain palmitic or stearic acid.

11. Process according to claim 9 wherein the ratio between said products and said supercritical carbon dioxide is 1:5 to 1:150 by weight and further wherein said products contain palmitic or stearic acid.

12. Process according to claim 9 wherein the ratio between said products and said supercritical carbon dioxide is 1:2.5 to 1:125 by weight and further wherein said products contain oleic or lauric acid.

13. Process according to claim 9 wherein the ratio between said products and said supercritical carbon dioxide is 1:5 to 1:15 to weight and further wherein said products contain oleic or lauric acid.

14. Process according to claim 1 wherein said products are polyester products and said extraction treatment is carried out continuously at a temperature at which said polyester products are liquid.

* * * * *

UNITED STATES PATENT AND TRADEMARK OFFICE
CERTIFICATE OF CORRECTION

PATENT NO. : 5,378,834
DATED : January 3, 1995
INVENTOR(S) : Kees Koerts, Age Bakker and Gerardus M. Vianen It is certified that error appears in the above-indentified patent and that said Letters Patent is hereby corrected as shown below:

Title page, under [56], References Cited, OTHER PUBLICATIONS, insert --PCT/US89/02,357, filed 29 October 1986, entitled "Supercritical Fluid Extraction of Animal Derived Materials", A. Kamarei, Int. Cl. C11B 1/10, CO7K 7/00, CO7H 1/06, 19/00--.

Column 1 Line 52 "4,3792,041" should read --3,792,041--.

Column 1 Line 58 "4,748,324" should read --3,748,324--.

Column 2 Line 20 "66" should read --55--.

Column 3 Line 19 "temperature < 31° C.;" should read --temperature > 31° C.;--.

Column 4 Line 36 "if" should read --is--.

Column 5 Line 33 "if" should read --is--.

UNITED STATES PATENT AND TRADEMARK OFFICE
CERTIFICATE OF CORRECTION

PATENT NO. : 5,378,834
DATED : January 3, 1995
INVENTOR(S) : Kees Koerts, Age Bakker and Gerardus M. Vianen It is certified that error appears in the above-indentified patent and that said Letters Patent is hereby corrected as shown below:

Column 6 Line 67 after "sucrose" insert --palmitate--.

Signed and Sealed this

Eighteenth Day of April, 1995

Attest:

BRUCE LEHMAN

Attesting Officer

Commissioner of Patents and Trademarks